(12) United States Patent
Arts et al.

(10) Patent No.: US 7,803,631 B2
(45) Date of Patent: Sep. 28, 2010

(54) PROCESS AND ARRANGEMENT FOR DETERMINING WATER CONTENT

(75) Inventors: Werner Arts, Berlin (DE); Berndt Martens, Bargteheide (DE)

(73) Assignee: LAR Process Analysers AG, Berlin (DE)

( * ) Notice: Subject to any disclaimer, the term of this patent is extended or adjusted under 35 U.S.C. 154(b) by 112 days.

(21) Appl. No.: 10/583,932

(22) PCT Filed: Dec. 6, 2004

(86) PCT No.: PCT/EP2004/013865

§ 371 (c)(1),
(2), (4) Date: Jun. 22, 2006

(87) PCT Pub. No.: WO2005/064329

PCT Pub. Date: Jul. 14, 2005

(65) Prior Publication Data

US 2008/0026482 A1    Jan. 31, 2008

(30) Foreign Application Priority Data

Dec. 22, 2003   (DE) ................................ 103 60 445

(51) Int. Cl.
*G01N 33/00*    (2006.01)
*B01J 19/00*    (2006.01)

(52) U.S. Cl. .................. 436/146; 436/114; 436/139; 436/106; 422/80; 422/78; 422/68.1; 422/50

(58) Field of Classification Search ................ 436/114, 436/146; 422/67, 80

See application file for complete search history.

(56) References Cited

U.S. PATENT DOCUMENTS

| 4,277,438 A | * | 7/1981 | Ejzak ........................... 422/80 |
| 5,292,666 A | * | 3/1994 | Fabinski et al. ............. 436/114 |
| 5,425,919 A | * | 6/1995 | Inoue et al. ................... 422/67 |

FOREIGN PATENT DOCUMENTS

| DE | 23 62 773 | 6/1975 |
| DE | 39 42 229 C2 | 7/1991 |
| DE | 41 15 425 C1 | 8/1992 |
| DE | 43 09 646 A1 | 9/1993 |
| DE | 43 44 441 C1 | 7/1995 |
| DE | 100 12 730 C1 | 7/2001 |
| EP | 0 512 238 | 11/1992 |
| EP | 0 684 471 | 5/1995 |
| EP | 0 730 153 | 9/1996 |
| JP | 09-178723 | 7/1997 |

* cited by examiner

*Primary Examiner*—Walter D Griffin
*Assistant Examiner*—Christine T Mui
(74) *Attorney, Agent, or Firm*—Dennison, Schultz & MacDonald; George H. Spencer

(57) ABSTRACT

Process for determination of a water content material, in particular organic carbon content and/or nitrogen, in which an aqueous sample is evaporated and combusted in at least one heating vessel equipped with a heating facility and the combustion product is fed in a transport gas flow to a detector for determination of the concentration of a gaseous compound of the water content material, characterised in that calibration is performed with a predetermined volume of a calibration gas which contains a predetermined concentration of the element corresponding to the water content material, in particular carbon and/or nitrogen.

12 Claims, 1 Drawing Sheet

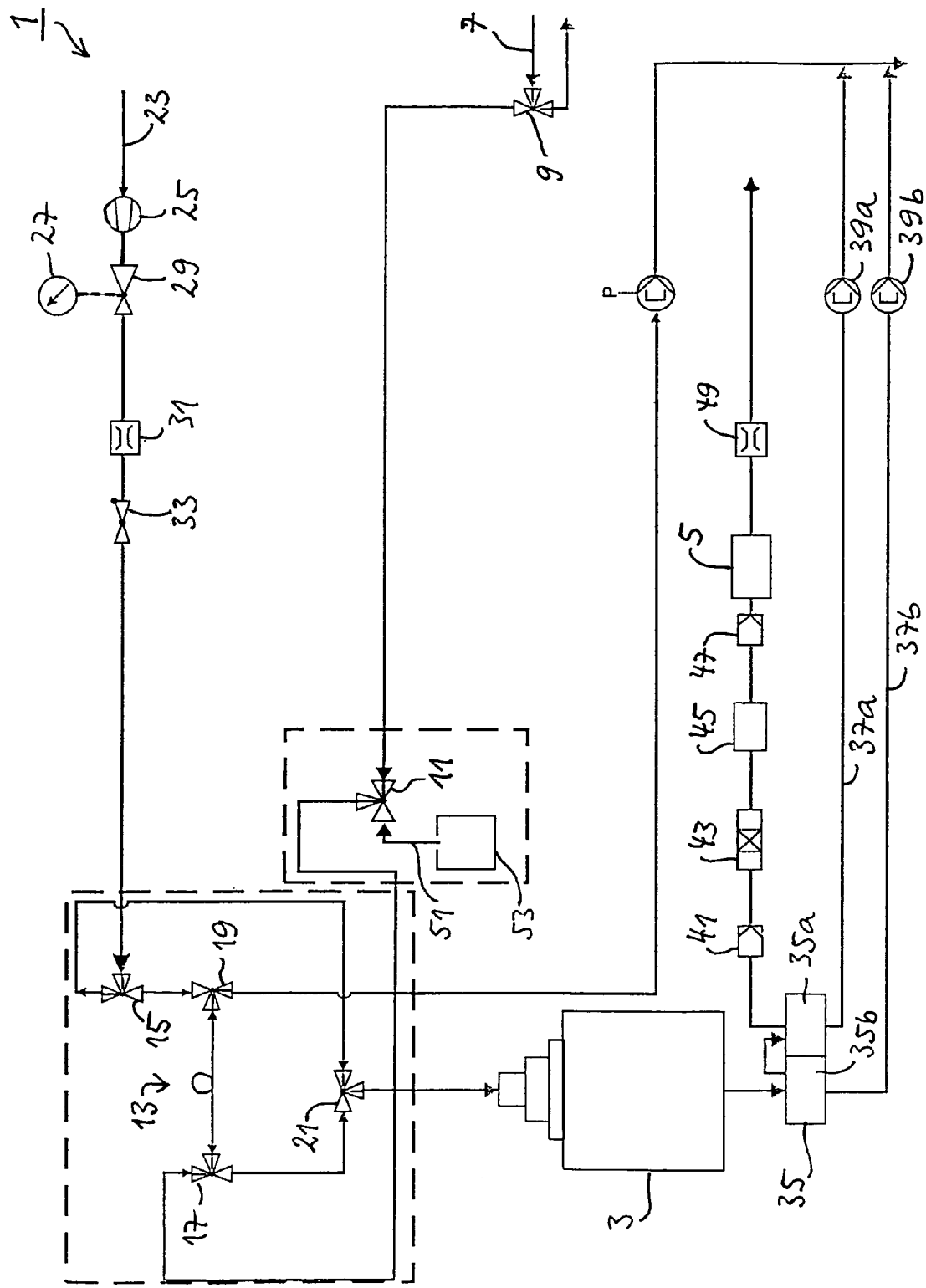

PROCESS AND ARRANGEMENT FOR DETERMINING WATER CONTENT

The invention concerns a process for determining water content according to the generic definition of claim 1 as well as an arrangement for carrying out the process.

It is known that, to determine the amount of certain water content materials, and thus the quality of water, a sample is vaporised and combusted in an atmosphere of an inert transport gas enriched with oxygen and the resulting combustion gas mixture is passed on to a detector suitable for the verification of carbon dioxide, nitrogen oxides, etc. Infrared detectors for the carbon content, special chemoluminescence detectors for the nitrogen content and so-called coulometric detectors for the halogenide content have proven themselves (among others).

The verification processes for determining organic contents—so-called TOC (total organic carbon)—based on combustion of a water sample, have attained widespread use. Usually, a small amount of water is fed with the transport gas to an oven preheated to a defined temperature, where it almost suddenly evaporates and combusts, and the combustion gas is fed to an NDIR $CO_2$ detector. Its measured $CO_2$ content is a measure of the water sample's carbon content.

One version of the process and an appropriate apparatus are the ones described in DE 43 44 441 C2. A modified arrangement for measuring very low TOC values—for example in highly pure water or solutions for medical applications—is described in EP 0 684 471 A2.

With this process, the TOC of interest is not automatically determined, but basically the total carbon (TC) content of the water, which embraces not only the TOC, but also the amount of inorganic carbon compounds (TIC=total inorganic carbon). These are therefore separated to determine the TOC in a previous separation step (co-called stripping); compare, for example, DE 39 42 229 C2 (with further literature references).

During separation of the inorganic carbon by stripping, a further problem arises in that organic carbon that can be stripped or which is volatile (POC or VOC=volatile organic carbon) is also removed from the sample. In DE 43 09 646 A1, therefore, a process and an analysis arrangement of the type sketched above are proposed in which the POC content is measured separately and, to obtain correct POC measurements, carbon compounds unintentionally also stripped are intercepted by a special adsorber agent.

In the case of the aforementioned kind of measurement processes and fixtures, calibration is necessary at certain intervals with calibration samples that contain an exactly known amount of the content material to be determined, for example to record long-term drift of the detectors and—if it exists—to be able to compensate for it by corresponding changes in the evaluation algorithm. There are industrial applications in which calibration should be performed at intervals that are not too long because the water added to them must conform uncompromisingly and reliably to maximum purity requirements. Thus, for example, in the pharmaceuticals industry, a production batch produced with extremely pure water must be rejected if its TOC content exceeds a certain value. If such an irregularity is detected during calibration of the measurement apparatus, the entire production volume since the last calibration must be rejected, which may lead to very high financial losses on the part of the manufacturer.

To avoid excessive abrupt pressure loads on the analysis apparatus as a result of detonation in the hot oven, the volumes of water samples fed to it must be made very small, which presumes the use of highly precise dosing systems. For the aforementioned calibrations with water samples containing a very slight and exactly defined amount of the water content material to be detected (so-called "zero water solutions"), this poses an additional problem, namely: Every minimal impurity in a vessel, dosing device, etc. used can falsify the result to a high degree during calibration. This aggravates the situation, which is problematic anyway, in which, in the case of zero-water concentrations of the relative content material (e.g. carbon) below 1 mg/l, exact mixing of the calibration solution and especially also the exactly graduated adjustment of diverse content concentrations is already a problem because the "dilution water" is also not completely pure.

Otherwise, the aforementioned calibration procedures using calibration or zero-water solutions also involve considerable amounts of work and call for the deployment of qualified specialist personnel and, moreover, there are relatively highly susceptible to interference due to ambient influences. Basically, ultra-clean room conditions have to be warranted in the so-called concentration range, including the appropriate air conditioning and personnel clothing.

The essential underlying object of the invention is to specify a low-cost process that is suitable for routine operation which features high measurement accuracy for the specific determination of water content, especially of TOC in highly pure water for pharmaceutical processes, as well as a apparatus for carrying out the process.

With regard to its process aspect, the object is solved by a process with the characteristics of claim 1 and, with regard to the apparatus aspect, with the characteristics of claim 8.

The invention includes the essential idea of fundamentally breaking with the previous practice in the case of the processing conforming to its genre, of no longer realising calibration with a sample in the same aggregate state as the measured sample—i.e. in a calibration or zero-water solution—but with a calibration gas. This idea is based on the consideration that a gas can also be doped with a previously determined volume of the content to be detected in a water sample to be tested (for example carbon). This also includes the consideration that such a calibration gas with a precisely pre-defined amount of doping can be produced relatively easily and at low cost with known technologies and can be handled to a high degree without ambient influences.

Considerable advantages are achieved with the invention, in particular in industrial processes in which ultra-pure water has to be available with very low and strictly limited concentrations of specific content materials, namely: In a simple way, relatively easy handling enables calibrations at short intervals without the need for complex measures for screening off ambient influences (ultra-clean room conditions, special clothing and behaviour on the part of personnel and the deployment of qualified analysis personnel). The gaseous calibration samples—in any case after establishment of the proposed process—are also available at low cost.

In a particularly significant variant of the process, a calibration gas with a predetermined $CO_2$ content is used to determine the amount of organic carbon (TOC) in measured samples. The application is particularly important in the pharmaceutical industry, where ultra-pure water with a strictly limited TOC content has to be used in many processes, and products that have been manufactured using water with a high TOC content have to be rejected.

In a preferred process variant, a predetermined volume of the calibration gas is set by filling a reservoir, in particular a section of hose, with a known volume under atmospheric pressure or with pressure compensation, which the flow of transport gas flows through after filling with the calibration gas. With this, loop injection processes and arrangements, which are known per se, in which also the measured samples are first of all gathered in an appropriate reservoir (section of hose) and then fed to the combustion oven, are improved by the invention and the aforementioned advantages are achieved. In a further advantageous variant of the process, it is planned to feed the calibration gas into the combustion vessel several times within the scope of the calibration procedure, each time including recording of the water content material in the detector. In this way, it is possible to conform to the common calibration specifications, which provide for statistical evaluation across several test points. In a continuation of this variant, the process is characterised by the fact that calibration takes place in several steps with a large number of different calibration gases containing different predetermined amounts of the element to be detected. This represents a particularly simple, fast and less susceptible realisation of the process of calibration (known per se and specified in DIN or EN specifications) at a minimum of five concentration points on a linear straight line.

As far as evaluation of the calibration measurements according to the invention is concerned, the range under a measured signal peak on the detector is expediently integrated and scaled to the predetermined content of the element in the calibration gas. In particular, it is scaled by the used of a predetermined correction factor.

The aspects of the invention relating to the fixture essentially correspond with the aforementioned process aspects and, as far as this is concerned, are not presented here once again. The calibration gases are made available in industrial common packaging, i.e. in compressed gas cylinders, which are known per se. In the case of the aforementioned loop variant, at least one such cylinder is capable of connection to a predetermined section of hose on the apparatus on the inlet side of the heating vessel (combustion oven); preferably, for realisation of the multi-point calibration also mentioned above, several gas cylinders containing different concentrations (ppm, ppw) of the content material can be optionally connected there. They can be connected easily by means of conventional shut-off valves or by the gas cylinders' shut-off and reducing valves, in conjunction also with multiple-way valves at the arrangement end.

For the aforementioned important application of TOC determination in process water (ultra-pure water), it is intended to link calibration gas cylinders containing a predetermined concentration of $CO_2$ in highly pure N2 or in highly pure air. It is self-evident that different calibration gas compositions have to be used for measurement arrangements intended for other water content materials.

Advantages and practicalities of the invention otherwise result from the dependent claims and the following description of a prevent variant with reference to the FIGURE.

The only FIGURE shows a schematic depiction of the arrangement according to the invention in an initial operating state.

The FIGURE shows a TOC measurement arrangement 1 for detecting the content of organic carbon in a process water sample, the core elements of which are a thermal reactor 3 for thermal disintegration of water samples and an infrared detector 5 for detecting the $CO_2$ content of the reaction products leaving the reactor 3 and thus for (indirect) determination of the TOC content in water samples 7. The water samples 7 first pass through an (optional) pressure reducing valve 9 and a multiple-way valve 11 into a dosing loop 13 and, during a measurement operation, are carried from there—with suitable settings of the multiple-way valves 15, 17, 19 and 21—by the transport or carrier gas flow 23 into the reactor 3 and are abruptly heated up and combusted there. The carrier gas flow 23 is routed via a feed pump 25 and a pressure reducing valve 29 equipped with a pressure measuring unit 27 and also a volume flow measuring unit 31 and a non-return valves 33 to the first multiple-way valve 15.

At the outlet end of the reactor 3, a reaction gas cooler 35 is first of all located, which has two stages 35a, 35b and out of which two condensed water flows 37a, 37b emerge, each of which is discharged via a peristalsis pump 39a, 39b. The reaction gas dewatered to this extent is then passed through an aerosol filter 41 and an acid trap 43 to a mass throughput control 45. From there, it finally passes through an air filter 47 to the aforementioned IR detector 5 and leaves the system through a volume flow measuring unit 49 located at the outlet end.

Instead of a water sample 7 serving as the measured sample, a calibration gas 51 can also be fed to the reactor in the carrier gas flow 23 to realise a calibration operation. To this end, a calibration gas cylinder 53 (shown symbolically here) is connected to the multiple-way valve. In a position of the multiple-way valve 11 that links its outlet to the subsequently connected multiple-way valve 17, a gaseous calibration sample 51 is then fed into the loop instead of a liquid measured sample. After this has been filled, by analogy to the normal measurement process—the calibration sample can be fed into the reactor by means of a suitable position of the multiple-way valves 15, 17, 19, and 21. There, it is transformed in the same way as a measured sample and the result of detection on the IR detector 5 is evaluated with an evaluation program tailored to the gaseous calibration sample. In the result of evaluation of the calibration measurement, the evaluation program for measured sample evaluation may also be modified to compensate for any zero line offset or similar occurring in the meantime. This ensures constant detection accuracy of the TOC measurement arrangement 1.

Realisation of the invention is not limited to this example and, instead, is possible in a large number of variants of the specific measurement arrangement in terms both of the water content materials to be detected and also of the (gaseous) calibration samples used.

The invention claimed is:

1. A batch process for water content material determination in a measurement apparatus, the process comprising: evaporating and combusting a predetermined amount of an aqueous sample automatically taken analysis in at least one heating vessel equipped with a heating facility, feeding the combustion product in a transport gas flow via sample transport pipes leading to a detector, determining the concentration of a gaseous compound of the water content material, and calibrating the apparatus, including the heating vessel, sample transport pipes and detector, with a predetermined amount of a calibrating gas which contains a predetermined concentration of the element corresponding to the water content material, said calibration gas, in the calibration step, being fed in the transport gas flow instead of the combustion product, the predetermined amount of calibration gas being set by filling a reservoir with one of a known volume of gas under atmospheric pressure or with pressure compensation, and the flow of transport gas, after filling with the calibration gas, being passed through the reservoir.

2. A process according to claim 1, wherein the water content material being determined is organic carbon content and/or nitrogen.

3. A process according to claim 1, wherein the calibration gas has a predetermined carbon dioxide content for determining the amount of organic carbon (TOC) in a plurality of measured samples.

4. A process according to claim 1, wherein measuring steps with the combustion products being fed in the transport gas flow are carried out alternating with calibration steps with the calibration gas being fed in the transport gas flow.

5. A process according to claim 1, wherein the reservoir is a section of a hose.

6. A process according to claim 1, wherein the calibration gas is fed into the heating vessel several times during a calibration step, and wherein during each such feeding, the water content material is recorded in the detector.

7. A process according to claim 6, where a calibration step comprises several sub-steps with a large number of different calibration gases containing different predetermined amounts of the element to be detected.

8. A process according to claim 1, wherein a range under a measured signal peak on the detector is integrated and scaled to the predetermined content of the element in the calibration gas.

9. A process according to claim 8, wherein a predetermined correction factor is used for scaling.

10. A process according to claim 1 applied to highly pure water for pharmaceutical application.

11. An apparatus for determining water content material comprising a measured sample feeding unit, a heating vessel having inlet and outlet ends, a transport gas source, a detector unit arranged at the outlet end of the heating vessel, a flow path linking the inlet end of the heating vessel to the transport gas source, the measured sample feeding until being connectible and lockable to the transport gas source, at least one calibration gas reservoir which is connectible to the flow path of the transport gas flow, switching means for connecting either the sample feeding unit or the calibration gas reservoir with the flow path of the transport gas, at least one gas cylinder containing a calibration gas and connected in lockable fashion to the flow path of the transport, the calibration gas having a predetermined carbon dioxide concentration, and a section of the transport flow path being a hose section having a predetermined volume, said gas cylinder being connectible to said hose section.

12. An apparatus according to claim 11, further comprising a plurality of gas cylinders containing the calibration gas in different concentrations, said gas cylinders being connectible to the transport flow path and being capable of being shut off individually.

* * * * *